(12) United States Patent
Yong et al.

(10) Patent No.: US 10,444,935 B2
(45) Date of Patent: Oct. 15, 2019

(54) USER INTERFACE DISPLAY METHOD

(71) Applicant: CAL-COMP BIG DATA, INC., New Taipei (TW)

(72) Inventors: Chia-Ming Yong, New Taipei (TW); Hung-Tai Hsu, New Taipei (TW); Ching-Sheng Tsai, New Taipei (TW)

(73) Assignee: CAL-COMP BIG DATA, INC., New Taipei (TW)

( * ) Notice: Subject to any disclaimer, the term of this patent is extended or adjusted under 35 U.S.C. 154(b) by 176 days.

(21) Appl. No.: 15/429,173

(22) Filed: Feb. 10, 2017

(65) Prior Publication Data

US 2018/0088778 A1    Mar. 29, 2018

(30) Foreign Application Priority Data

Sep. 29, 2016 (TW) .............................. 105131407 A

(51) Int. Cl.
| | |
|---|---|
| *G06F 3/048* | (2013.01) |
| *G06F 3/0481* | (2013.01) |
| *G06F 3/0482* | (2013.01) |
| *G06F 3/0484* | (2013.01) |
| *G16H 40/60* | (2018.01) |
| *G16H 50/30* | (2018.01) |

(52) U.S. Cl.
CPC ........ *G06F 3/04817* (2013.01); *G06F 3/0482* (2013.01); *G06F 3/04847* (2013.01); *G16H 40/60* (2018.01); *G16H 50/30* (2018.01); *G06F 2203/04803* (2013.01)

(58) Field of Classification Search
CPC ... G01G 19/50; A63F 3/0423; G06F 19/3475; G06F 3/0481; G16H 20/60
See application file for complete search history.

(56) References Cited

U.S. PATENT DOCUMENTS

| | | | | |
|---|---|---|---|---|
| 2004/0001105 | A1* | 1/2004 | Chew | G06F 3/0482 715/817 |
| 2010/0156045 | A1* | 6/2010 | Kahn | A63F 3/0423 273/153 R |
| 2012/0194547 | A1* | 8/2012 | Johnson | G06T 11/00 345/632 |
| 2014/0169217 | A1* | 6/2014 | Coroy | G01G 19/50 370/254 |
| 2015/0226747 | A1* | 8/2015 | Kodama | G06F 19/3475 702/19 |
| 2017/0165526 | A1* | 6/2017 | Bakun | G06Q 30/0279 |
| 2017/0352289 | A1* | 12/2017 | Israetel | G01G 19/50 |

FOREIGN PATENT DOCUMENTS

| | | |
|---|---|---|
| TW | 201145138 | 12/2011 |
| TW | 201524455 | 7/2015 |
| TW | 201619803 | 6/2016 |

OTHER PUBLICATIONS

"Office Action of Taiwan Counterpart Application", dated Feb. 20, 2017, p. 1-p. 5, in which the listed references were cited.

* cited by examiner

*Primary Examiner* — Haoshian Shih
(74) *Attorney, Agent, or Firm* — JCIPRNET

(57) ABSTRACT

A user interface display method is provided. The method includes: displaying at a first location a current body type information related to a user; displaying a plurality of icons at a plurality of second locations adjacent to the first location respectively; when receiving a first input operation corresponding to the plurality of icons, displaying a first body type information of a plurality of body type information at the first location.

10 Claims, 12 Drawing Sheets

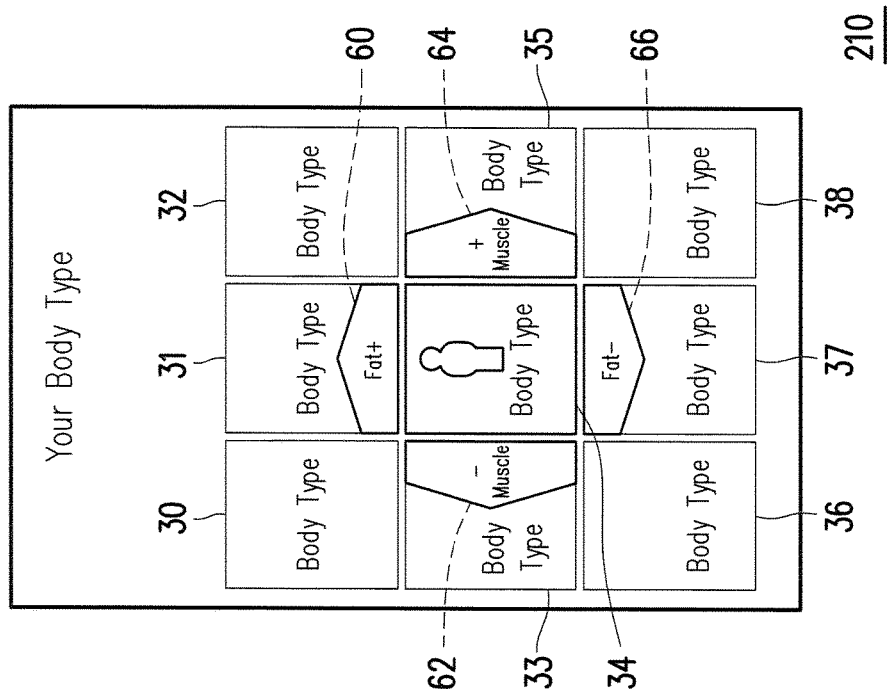

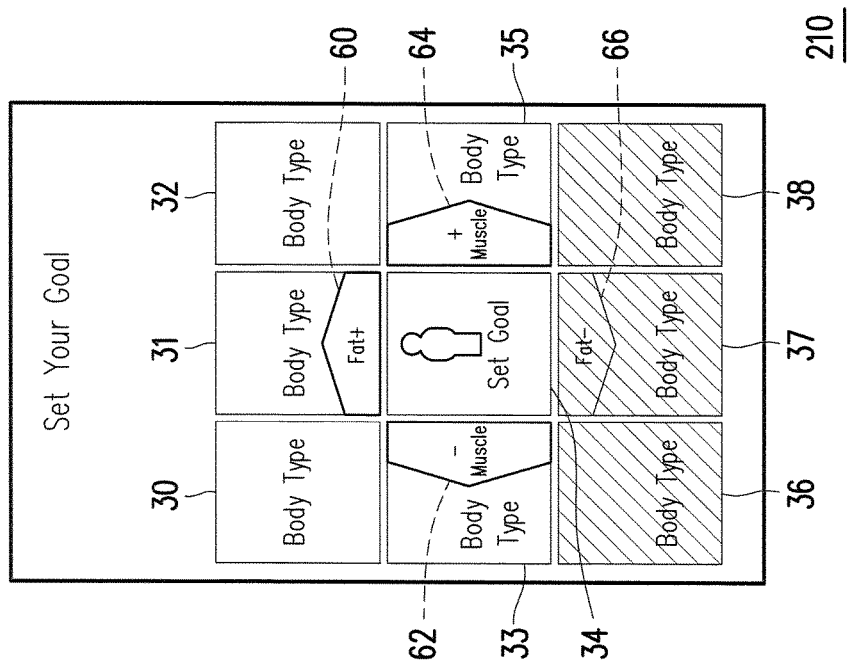

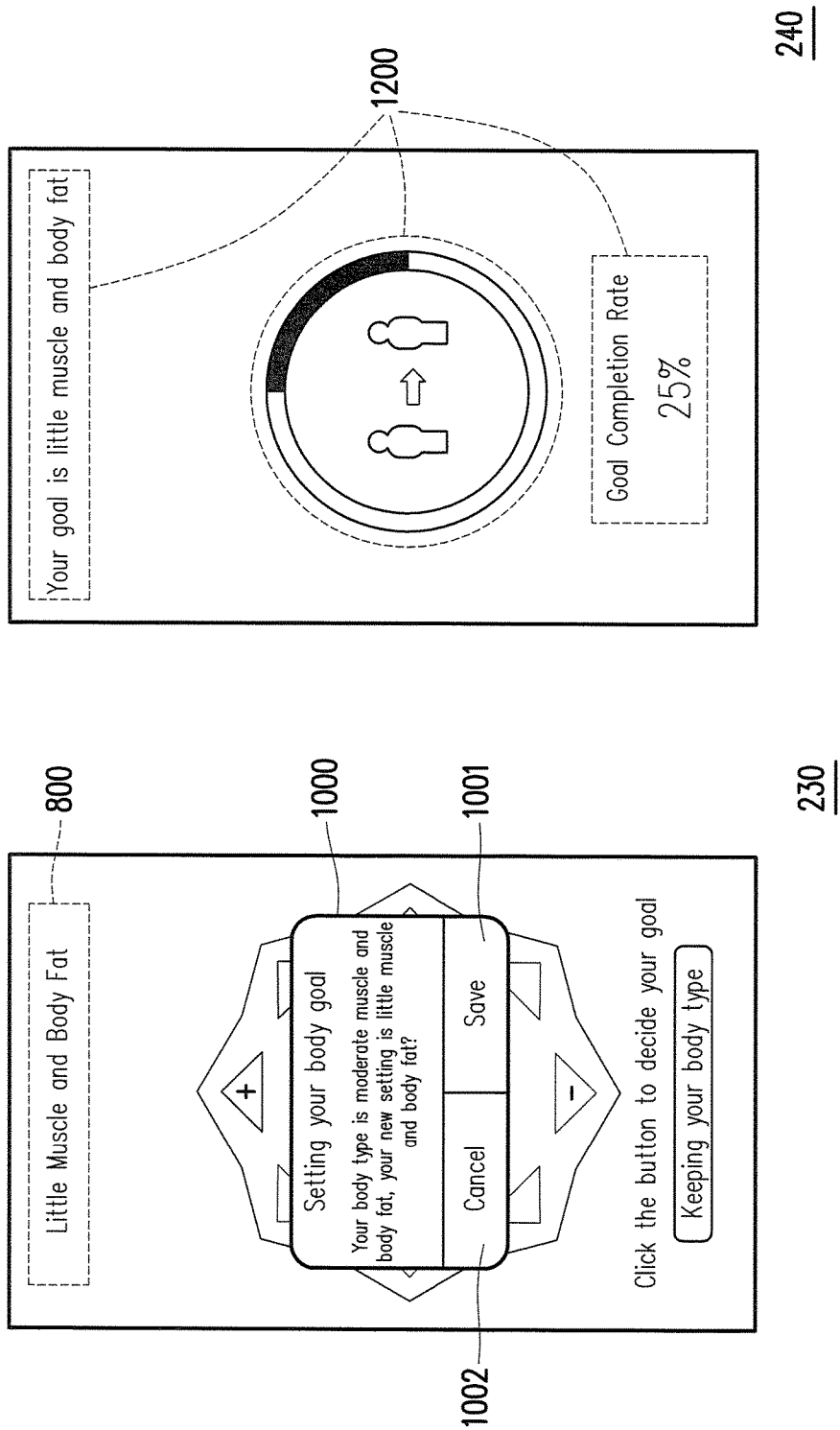

USER INTERFACE DISPLAY METHOD

CROSS-REFERENCE TO RELATED APPLICATION

This application claims the priority benefit of Taiwan application serial no. 105131407, filed on Sep. 29, 2016. The entirety of the above-mentioned patent application is hereby incorporated by reference herein and made a part of this specification.

FIELD OF THE INVENTION

The invention relates to a user interface display method, and particularly to a method for displaying and operating the user interface.

DESCRIPTION OF RELATED ART

Due to the growing popularity of fitness programs, people tend to work out for creating an ideal body type. At present, however, users are not able to learn different body types effectively through any existing method or application program, and the users cannot figure out how to change their current body types to target body types. For instance, the users may not know their body types and may not be aware of how to gain or lose body fat or muscle mass in order to obtain the target body type.

SUMMARY OF THE INVENTION

The invention provides a user interface display method that allows users to clearly know how to shape their bodies and assists the users in adjusting their body types to ideal body types in an effective manner.

According to an embodiment of the invention, a user interface display method is provided, and the method is adapted for an electronic device having a display unit, an input unit, and a processing unit. The method includes: displaying at a first location a current body type information related to a user by the display unit; respectively displaying by the display unit a plurality of icons at a plurality of second locations adjacent to the first location; when receiving a first input operation corresponding to the icons, displaying a first body type information of a plurality of body type information at the first location by the display unit.

In an embodiment of the invention, the first input operation is performed to input information of a first direction corresponding to the current body type information, and the user interface display method further includes: when the input unit receives a second input operation corresponding to the first body type information the input unit, setting the first body type information as a target body type information by the processing unit; displaying the current body type information at the first location by the display unit, displaying the icons at the second locations by the display unit, and displaying at a third location a first prompt information corresponding to the target body type information by the display unit. Here, the third location is in the first direction corresponding to the target body type information.

In an embodiment of the invention, the step of displaying at the first location the current body type information related to the user by the display unit includes: displaying by the display unit the current body type information in a first block at the first location; respectively displaying a plurality of second body type information of the plurality of body type information in a plurality of second blocks at a plurality of fourth locations by the display unit. Here, the fourth locations are adjacent to the first location.

In an embodiment of the invention, the fourth locations include the second locations.

In an embodiment of the invention, the step of respectively displaying the icons at the second locations includes: respectively displaying the icons in a plurality of third blocks in the second blocks at the second locations by the display unit.

In an embodiment of the invention, if a fourth block in the second blocks fails to correspond to a third body type information of the body type information, a second prompt information is displayed in the fourth block by the display unit.

In an embodiment of the invention, the step of displaying at the first location the first body type information of the body type information includes: displaying by the display unit the first body type information in the first block; respectively displaying by the display unit a plurality of fourth body type information of the body type information in the second blocks.

In an embodiment of the invention, the step of displaying the current body type information at the first location, displaying the icons at the second locations, and displaying at the third location the first prompt information corresponding to the target body type information includes: displaying by the display unit the current body type information in the first block; respectively displaying by the display unit the second body type information of the body type information in the second blocks; respectively displaying by the display unit the first prompt information in a fifth block in the second blocks corresponding to the first direction of the current body type information.

In an embodiment of the invention, if a fifth location at the second locations fails to correspond to a fifth body type information of the body type information, a third prompt information is displayed on a first icon of the icons corresponding to the fifth location by the display unit.

In an embodiment of the invention, the user interface display method further includes: displaying a status information by the display unit, wherein the status information represents a degree of completion achieved by changing from a first body type corresponding to the current body type information to a second body type corresponding to the target body type information.

In view of the above, the current body type information related to a user can be displayed through performing the user interface display method provided herein. After the user sets up the target body type information, the current body type information related to the user and the prompt information related to the target body type information may be displayed in the user interface. Thereby, the user may know more about his or her body type and may be aware of how to change the current body type to the target body type (e.g., gain/lose body fat or gain/lose muscle mass). Besides, through applying the user interface display method, the status information is also displayed, such that the user is able to learn what should be done in order to obtain the target body type.

To make the above features and advantages of the invention more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

FIG. 2A and FIG. 2B are schematic diagrams illustrating that an electronic device displays a current body type information related to a user according to an embodiment of the invention.

FIG. 4A and FIG. 4B are schematic diagrams illustrating that the displayed body type information is on the edge of a matrix according to an embodiment of the invention.

FIG. 10 is a schematic diagram of setting a target body type information according to an embodiment of the invention.

FIG. 11 is a schematic diagram of displaying a status information according to an embodiment of the invention.

DESCRIPTION OF EMBODIMENTS

Figure 1:
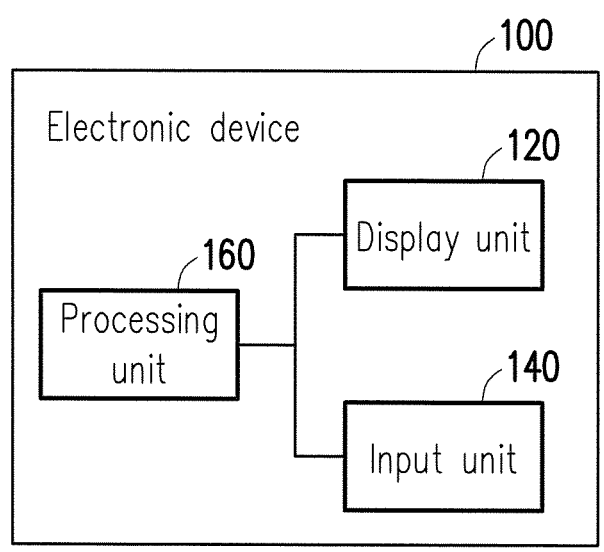
FIG. 1 is a block diagram showing an electronic device according to an embodiment of the invention.

FIG. 1 is a block diagram showing an electronic device according to an embodiment of the invention. With reference to FIG. 1, an electronic device 100 provided in the present embodiment includes a processing unit 120, an input unit 140, and a processing unit 160. The electronic device 100 is, for instance, a mobile phone, a tablet computer, a notebook computer, and so on, which should not be construed as a limitation to the invention.

The display unit 120 is a display device capable of performing a display function in a display region of the electronic device 100. The display unit 120 may be a liquid crystal display (LCD), a light-emitting diode display (LED), a field emission display (FED), or other types of displays which may perform display functions.

The input unit 140, for example, is an input device that may receive operations of a user, such as a mouse, a keyboard, a joystick, a touch pad, etc. Besides, the input unit 140 may also be a resistive touch sensing device, a capacitive touch sensing device, or touch sensing devices of other types that may be integrated with the display unit 120 of the electronic device 100 to form a touch screen.

The processing unit 160 is connected to the display unit 120 and the input unit 140 and may be a central processing unit (CPU), a programmable microprocessor for general use or special use, a digital signal processor (DSP), a programmable controller, an application specific integrated circuit (ASIC), other similar devices, or a combination of the foregoing.

In the present embodiment, the electronic device 100 further includes a storage unit (not shown) that stores a plurality of code snippets. After the code snippets are installed, they are executed by the processing unit 160. For example, the storage unit includes a plurality of modules, and each operation of the electronic device 100 can be performed by these modules. Each module includes one or more code snippets. However, the invention is not limited thereto, and each operation of the electronic device 100 may also be implemented by other hardware.

Several embodiments are provided below to illustrate the user interface display method described herein.

First Exemplary Embodiment

FIG. 2A and FIG. 2B are schematic diagrams illustrating that an electronic device displays a current body type information related to a user according to an embodiment of the invention.

With reference to FIG. 2A and FIG. 2B, in FIG. 2A, the storage unit of the electronic device 100 may store 25 body type information (i.e., body type information A to body type information Y) in advance. The 25 body type information may logically correspond to a 5×5 matrix 200, and each of the 25 body type information may logically correspond to one element in the matrix 200. For instance, the body type information A corresponds to the element in the first column and the first row of the matrix 200, the body type information B corresponds to the element in the second column and the first row of the matrix 200, the body type information F corresponds to the element in the first column and the second row of the matrix 200, and the rest can be deduced from the above. Specifically, the amount of the body type information and the size of the matrix 200 are not limited in the invention; in other exemplary embodiments, the electronic device 100 can store more or less body type information, and the matrix 200 may be larger or smaller.

In the present embodiment, the processing unit 160 can obtain the physiological information related to the user and set one body type information in the matrix 200 as the current body type information related to the user according to the physiological information related to the user. For instance, the user may input his or her physiological information through the input unit 140, and the physiological information may be body height, body weight, gender, age, and so forth. After the processing unit 160 receives the physiological information, the processing unit 160 calculates the body fat ratio of the user according to the physiological information and associates the calculated body fat ratio with one of the body type information A to Y. Note that said physiological information, the way to acquire the physiological information, and the way to associate the user's physiological information with one of the body type information are not limited in the invention. Besides, in this exemplary embodiment, the body type information is the body fat ratio, for instance. However, in another embodiment of the invention, the body type information may be the information related to the body type of a human being.

As shown in FIG. 2A, if the processing unit 160 sets the body type information M as the current body type information related to the user, the display unit 120 may, as shown in FIG. 2B, display the contents of the body type information M in a block 34 (also referred to as the first block) in a user interface 210 at a first location. Besides, in the matrix 200, the body type information around the body type information M is respectively displayed in the blocks around the block 34 in the user interface 210.

Specifically, in the user interface 210, the contents of the body type information H are displayed in a block 31 above the current body type information (i.e., the block 34), the contents of the body type information L are displayed in a block 33 on the left-hand side of the current body type information (i.e., the block 34), the contents of the body type information N are displayed in a block 35 on the right-hand side of the current body type information (i.e., the block 34), and the contents of the body type information R are displayed in a block 37 below the current body type information (i.e., the block 34).

Additionally, in the user interface 210, the contents of the body type information G are displayed in a block 30 on the upper-left side of the current body type information (i.e., the block 34), the contents of the body type information I are displayed in a block 32 on the upper-right side of the current body type information (i.e., the block 34), the contents of the body type information Q are displayed in a block 36 on the lower-left side of the current body type information (i.e., the block 34), and the contents of the body type information S are displayed in a block 38 on the lower-right side of the current body type information (i.e., the block 34).

In the user interface 210, the locations above, on the left side of, on the right side of, below, on the upper-left side of, on the upper-right side of, on the lower-left side of, and on the lower-right side of the current body type information may be collectively referred to as the "fourth locations", and the body type information displayed at the fourth locations (e.g., the body type information H, L, N, R, G, I, Q, and S) may be collectively referred to as the "second body type information". In addition, the blocks 30, 31, 32, 33, 35, 36, 37, and 38 may be collectively referred to as the "second blocks". That is, the second blocks at the fourth locations are adjacent or surround the block 34 at the first location.

The display unit 120 also displays icons 60, 62, 64, and 66 at locations above, on the left side of, on the right side of, and below the block 34. Specifically, the locations above, on the left side of, on the right side of, and below the block 34 may be collectively referred to as the "second locations", and the second locations are adjacent or surround the block 34 at the first location. The fourth locations include said second locations. In the present embodiment, the icon 60 is displayed in the block 31 that displays the body type information H, the icon 62 is displayed in the block 33 that displays the body type information L, the icon 64 is displayed in the block 35 that displays the body type information N, and the icon 66 is displayed in the block 37 that displays the body type information R. Note that the blocks 31, 33, 35, and 37 may be collectively referred to as the "third blocks".

Figure 2C:
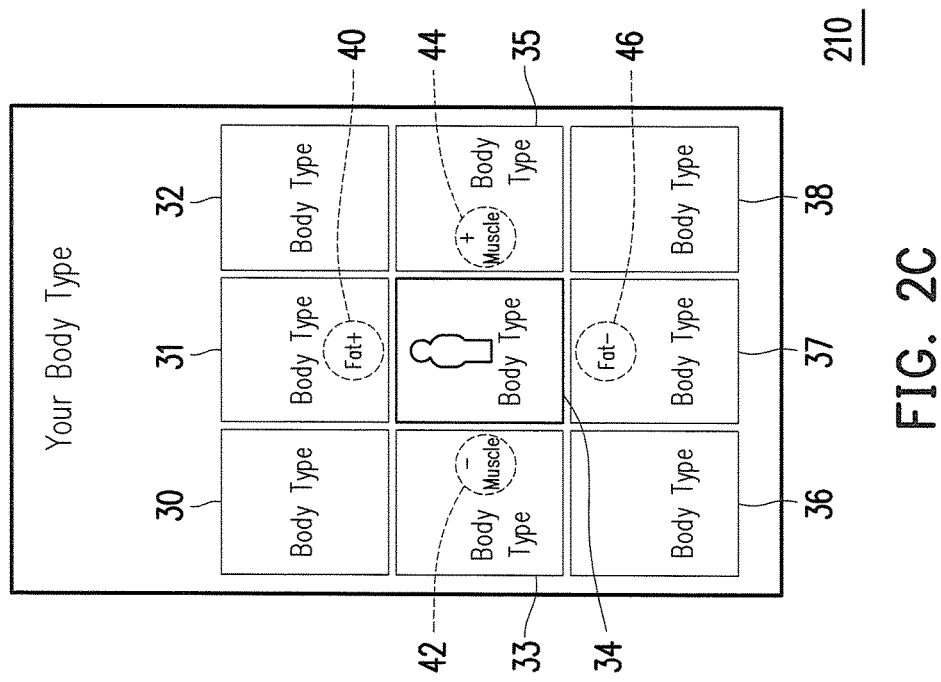
FIG. 2C is a schematic diagram illustrating that an electronic device displays icons according to an embodiment of the invention.

The way to display the icons is not limited in the invention. FIG. 2C is a schematic diagram illustrating that an electronic device displays icons according to an embodiment of the invention. Different from the icons represented by arrows in FIG. 2B, the icons 40, 42, 44, and 46 depicted in FIG. 2C and described in the present embodiment may be represented merely by texts and not by arrows. However, in other embodiments, the icons may be displayed in other forms, and the way to display the icons should not be construed as a limitation to the invention.

As shown in FIG. 2A and FIG. 2B, in this embodiment, the icons 60 and 66 are relevant to the amount of body fat, and the icons 62 and 64 are relevant to the amount of muscle. The user of the electronic device 100 may perform the input operation according to the icons 60, 62, 64, and 66, so as to observe other body type information. For instance, if the current body type information related to the user is the body type information M, the user may perform the input operation (e.g., clicking the icon 60) corresponding to the icon 60 through the input unit 140. The display unit 120 then displays the body type information H in which the amount of body fat is one level higher than that in the body type information M. Similarly, the user may perform the input operation (e.g., clicking the icon 66) corresponding to the icon 66 through the input unit 140. The display unit 120 then displays the body type information R in which the amount of body fat is one level lower than that in the body type information M. The user may also perform the input operation (e.g., clicking the icon 62) corresponding to the icon 62 through the input unit 140. The display unit 120 then displays the body type information L in which the amount of muscle is one level lower than that in the body type information M. Similarly, the user may perform the input operation (e.g., clicking the icon 64) corresponding to the icon 64 through the input unit 140. The display unit 120 then displays the body type information N in which the amount of muscle is one level higher than that in the body type information M. The input operations corresponding to the icons 60, 62, 64, and 66 may be performed together or individually, and the user can perform the input operations according to the icons 60, 62, 64, and 66 to observe other body type information and further select the target body type information.

Figures 3A, 3B:
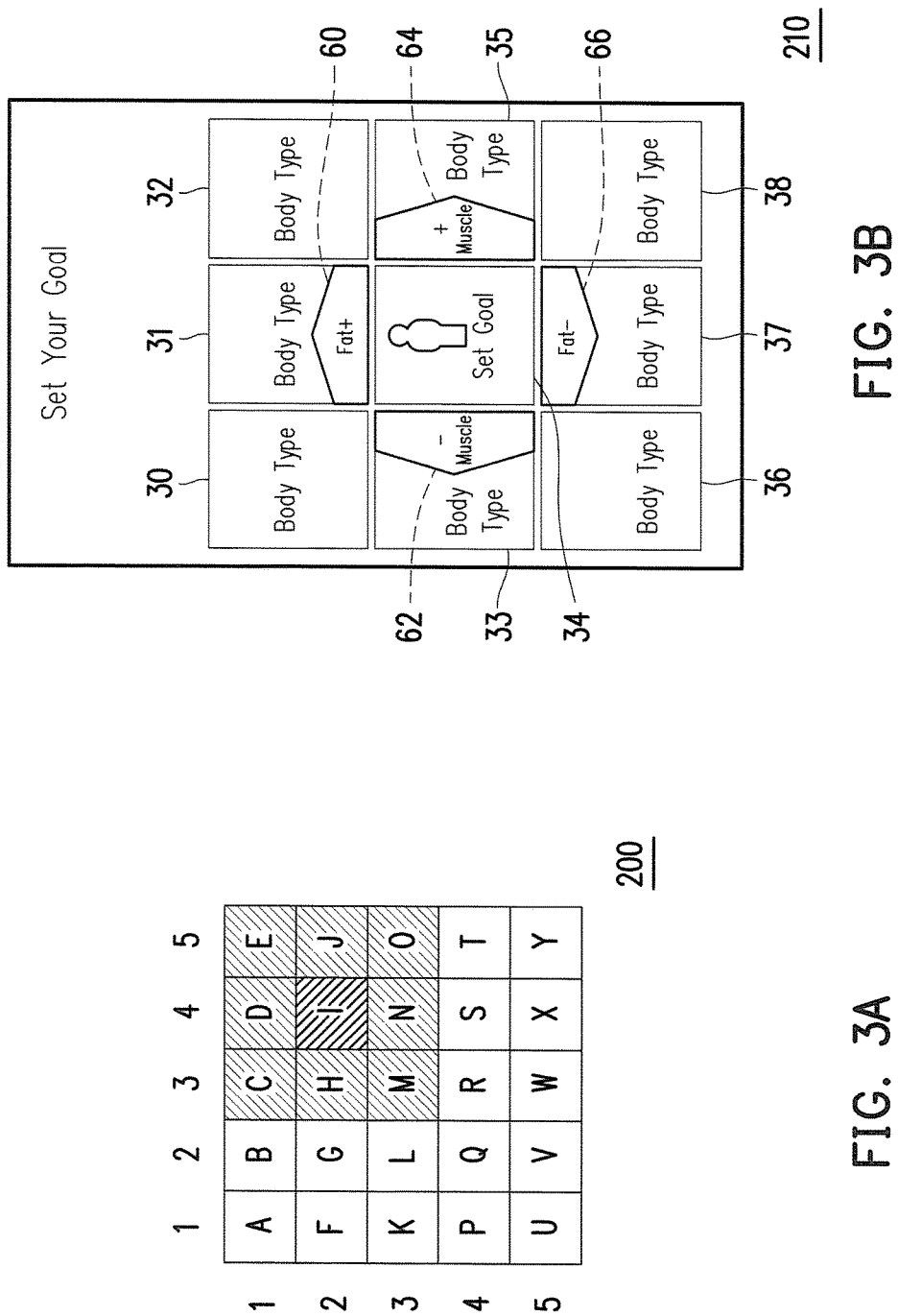
FIG. 3A and FIG. 3B are schematic diagrams of selecting a target body type information according to an embodiment of the invention.

FIG. 3A and FIG. 3B are schematic diagrams of selecting a target body type information according to an embodiment of the invention.

With reference to FIG. 3A and FIG. 3B that follow FIG. 2A and FIG. 2B, if the current body type information related to the user is the body type information M, the user may perform the first input operation through the input unit 140, as shown in FIG. 3A and FIG. 3B The first input operation includes the input operation (e.g., clicking the icon 60) corresponding to the icon 60 and the input operation (e.g., clicking the icon 64) corresponding to the icon 64. In other words, according to the present exemplary embodiment, the first input operation is performed to input the information correspondingly at the upper-right side of the current body type information (i.e., the first direction).

According to the first input operation, the processing unit 160 displays the body type information I at the upper-right side of the current body type information (i.e., the body type information M) in the block 34 in the user interface 210 in the matrix 200. Besides, in the matrix 200, the body type information around the body type information I is respectively displayed in the blocks around the block 34 in the user interface 210.

Specifically, the contents of the body type information C are displayed in the block 30 in the user interface 210, the contents of the body type information D are displayed in the block 31 in the user interface 210, the contents of the body type information E are displayed in the block 32 in the user interface 210, the contents of the body type information H are displayed in the block 33 in the user interface 210, the contents of the body type information J are displayed in the block 35 in the user interface 210, the contents of the body type information M are displayed in the block 36 in the user interface 210, the contents of the body type information N are displayed in the block 37 in the user interface 210, and the contents of the body type information O are displayed in the block 38 in the user interface 210. Besides, the icons 60, 62, 64, and 66 are still respectively displayed in the blocks 31, 33, 35, and 37 in the user interface 210. The body type information C, D, E, H, J, M, N, and O may be collectively referred to as the "fourth body type information".

That is, the first input operation is performed to enable the display unit 120 to display the body type information I at the upper-right side of the current body type information M in the block 34 in the user interface 210.

Specifically, in an exemplary embodiment, when the user performs the input operation, which causes the body type information displayed in the block 34 in the user interface 210 to be located on the edge or in the corner of the matrix 200, the display unit 120 displays a prompt information to remind the user that the body type information in some blocks in the user interface 210 cannot be set as the target body type information.

FIG. 4A and FIG. 4B are schematic diagrams illustrating that the displayed body type information is on the edge of a matrix according to an embodiment of the invention.

With reference to FIG. 4A and FIG. 4B, in the present embodiment, after the user executes the input operation, which causes the body type information displayed in the block 34 in the user interface 200 to be the body type information W in the matrix 200, the body type information Q, R, S, V, and X around the body type information W is respectively displayed in the blocks 30, 31, 32, 33, and 35 around the block 34 in the user interface 210. However, in the matrix 200, there is no body information below the body type information W that may correspond to the block 37 (i.e., the fourth block) in the user interface 210, and therefore the display unit 120 displays a prompt information (i.e., the second prompt information) in the block 37. That is to say, if the block 37 fails to correspond to a body type information (i.e., the third body type information) in the matrix 200, the display unit 120 displays a prompt information in the block 37. Here, the prompt information, for example, is shown by displaying the block 37 and the icon 66 in certain color. The way to display the prompt information far exceeds to what has been described herein.

Similarly, in the matrix 200, there is no body type information on the lower-left side and the lower-right side of the body type information W that may correspond to the blocks 36 and 38 in the user interface 210, and therefore the display unit 120 displays a prompt information in the blocks 36 and 38. That is, if the blocks 36 and 38 fail to correspond to the body type information in the matrix 200, the display unit 120 displays prompt information in the blocks 36 and 38. Here, the prompt information is the blocks 36 and 38 displayed in certain color. The way to display the prompt information far exceeds to what has been described herein.

Figures 5A, 5B:
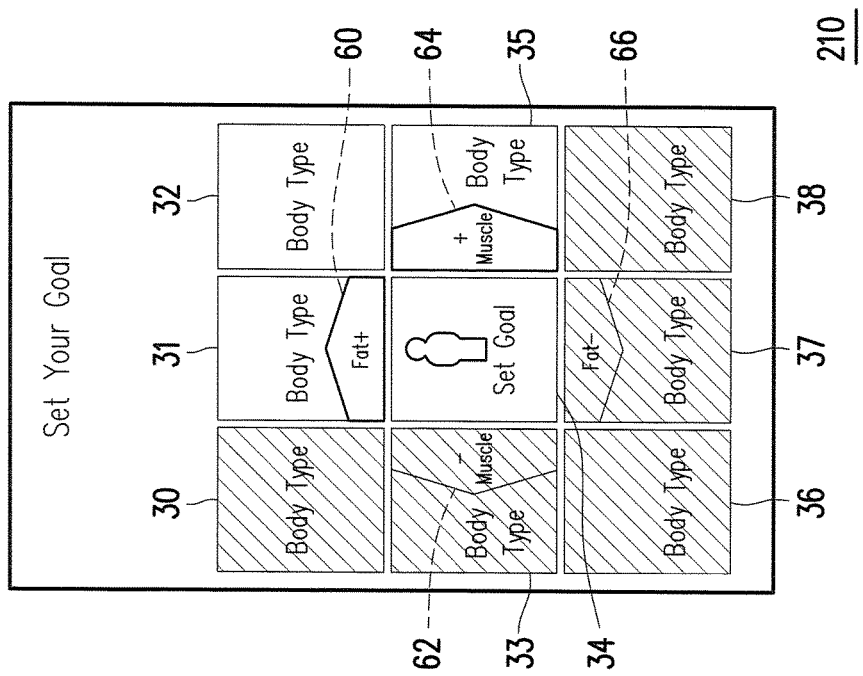
FIG. 5A and FIG. 5B are schematic diagrams illustrating that the displayed body type information is in the corner of a matrix according to an embodiment of the invention.

FIG. 5A and FIG. 5B are schematic diagrams illustrating that the displayed body type information is in the corner of a matrix according to an embodiment of the invention.

With reference to FIG. 5A and FIG. 5B, in the present embodiment, after the user executes the input operation, which causes the body type information displayed in the block 34 in the user interface 200 to be the body type information U in the matrix 200, the body type information P, Q, and V around the body type information U is respectively displayed in the blocks 31, 32, and 35 around the block 34 in the user interface 210. However, in the matrix 200, there is no body information on the upper-left side of, on the left side of, on the lower-left side of, below, and on the lower-right side of the body type information U that may correspond to the blocks 30, 33, 36, 37, and 38 in the user interface 210, and therefore the display unit 120 displays prompt information in the blocks 30, 33, 36, 37 and 38. Here, the prompt information is the blocks 30, 33, 36, 37, and 38 as well as the icons 62 and 66 which are displayed in certain color. The way to display the prompt information far exceeds to what has been described herein.

In the present exemplary embodiment, if the current body type information related to the user is displayed in the block 34 in the user interface 210, the user is able to perform said input operation, such that the block 34 displays the non-current body type information of the body type information A-Y. After said input operation is performed, the user can set the non-current body type information displayed in the block 34 as the target body type information.

For instance, as shown in FIG. 3A and FIG. 3B, when the user performs the first input operation, which causes the contents of the body type information I to be displayed in the block 34 in the user interface 210, the user can perform another input operation (i.e., a second input operation) through the input unit 140. The processing unit 160 can then set the body type information I as the target body type information. The second input operation is, for instance, to click the block 34. However, the way to perform the second input operation far exceeds to what has been described herein.

After the second input operation is completely performed, and the body type information I is already set as the target body type information, the display unit 120 displays the current body type information (i.e., the body type information M) related to the user at the first location, displays the icons 60-64 at the second locations, and displays the prompt information (i.e., the first prompt information) corresponding to the target body type information at a third location. The third location is in the first direction corresponding to the current body type information.

Figures 6A, 6B:
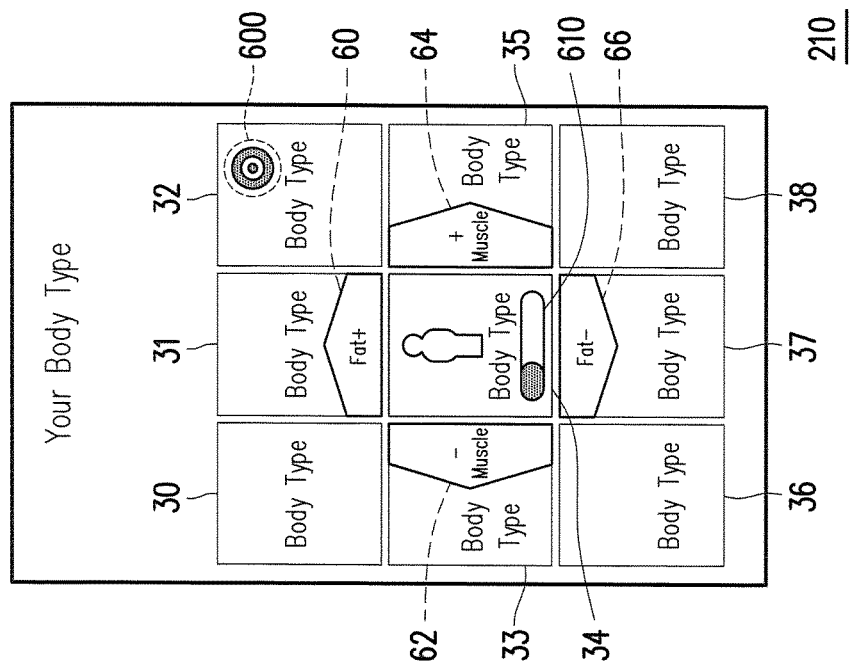
FIG. 6A and FIG. 6B are schematic diagrams of setting a target body type information and displaying a corresponding prompt information according to an embodiment of the invention.

FIG. 6A and FIG. 6B are schematic diagrams of setting a target body type information and displaying a corresponding prompt information according to an embodiment of the invention.

Please refer to FIG. 6A and FIG. 6B which follow FIG. 3A and FIG. 3B. After the second input operation is completely performed, and the body type information I is already set as the target body type information, the display unit 120 displays the current body type information (i.e., the body type information M) related to the user in the block 34 in the user interface 210. The display unit 120 also displays icons 60, 62, 64, and 66 in the blocks 31, 33, 35, and 37 (i.e., at the second locations). Besides, the display unit 120 also displays the prompt information 600 (i.e., the first prompt information) in the block 32 (i.e., the fifth block) on the upper-right side of the block 34 (i.e., in the first direction), and the location on the upper-right side of the block 34 may be referred to as the third location. If the user selects one of the body type information D, E, and J as the target body type information, the current body type information (i.e., the body type information M) related to the user can be displayed in the block 34 in the user interface 210, and a prompt information is displayed in the block 32 on the upper-right side of the block 34.

According to the exemplary embodiment depicted in FIG. 6A and FIG. 6B, after the target body type information is set, the display unit 120 may further display a status information 610. The status information 610 represents a degree of completion achieved by changing from a body type (i.e., the first body type) corresponding to the current body type information (i.e., the body type information M) to a body type (i.e., the second body type) corresponding to the target body type information (i.e., the body type information I). In the present embodiment, the status information 610 is displayed in form of a status bar. However, the invention is not limited thereto, and the status information 610 may also be displayed in another manner.

Note that the user may periodically input his or her current physiological information, and the processing unit 160 calculates the level of completion by comparing the current physiological information with the preset target body type information. In addition, the corresponding status information 610 is displayed by the display unit 120. If the physiological information related to the user is slightly changed (e.g., the body weight is reduced), the changes to the body type may not be apparent, and thus the body type information related to the user may still be the current body type information (i.e., the body type information M) that is previously set. However, the slight change to the physiological information allows the processing unit 160 to calculate the degree of completion according to the amount of such change to the physiological information (e.g., the reduced weight). Here, the degree of completion is calculated by comparing a body type (i.e., the first body type) corresponding to the current body type information (i.e., the body type M) which is set previously with a body type (i.e., the second body type) corresponding to the target body type information (i.e., the body type information I). The way to calculate the level of completion is not limited in the invention. FIG. 6B illustrates that the status information 610 is displayed in the block 34 in the user interface 210. However, the invention is not limited thereto. In other embodiments, the status information 610 may not be displayed in any of the blocks 30-38. Besides, the status information 610 may also be displayed in another user interface different from the user interface 210.

In light of the foregoing, according to the first exemplary embodiment of the invention, a number of body type information is displayed in the blocks 30-38 in the user interface 210. The current body type information related to the user may be displayed in the block 34. When the user performs the input operation, the corresponding body type information in the matrix 200 may be displayed in the block 34 according to the input operation. After the user sets up the target body type information, the current body type information related to the user may be displayed in the block 34, and the prompt information related to the target body type information may be displayed in the corresponding block in the user interface. Through the information displayed in the user interface 210, the user may know more about his or her body type and may be aware of how to change the current body type to the target body type (e.g., gain/lose body fat or gain/lose muscle mass). Besides, the status information 610 displayed by the display unit 120 allows the user to learn what should be done subsequently in order to obtain the target body type.

Second Exemplary Embodiment

Different from the user interface provided in the first exemplary embodiment, the user interface provided in the second exemplary embodiment does not display plural blocks.

Figures 7A, 7B:
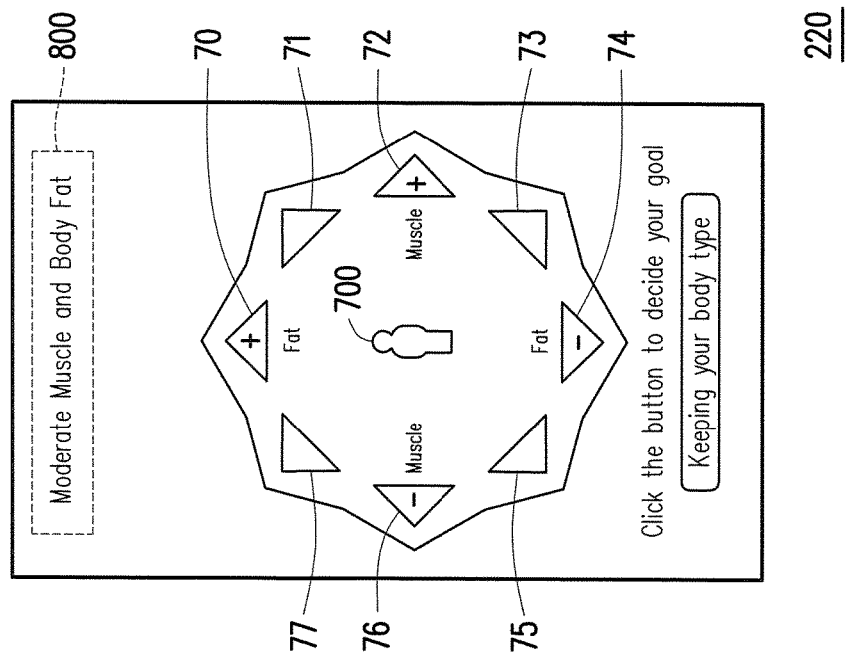
FIG. 7A and FIG. 7B are schematic diagrams illustrating that an electronic device displays a current body type information related to a user according to an embodiment of the invention.

FIG. 7A and FIG. 7B are schematic diagrams illustrating that an electronic device displays a current body type information related to a user according to an embodiment of the invention.

Please refer to FIG. 7A and FIG. 7B, and the matrix 200 depicted in FIG. 7A is identical to the matrix 200 depicted in FIG. 2A. If the processing unit 160 sets the body type information M as the current body type information related to the user, the display unit 120 may, as shown in FIG. 7B, display the current body type information 700 corresponding to the body type information M at a location (i.e., the first location) right in the center of the user interface 220. The display unit 120 also displays the descriptions associated with the body type information M in a region 800.

In the present embodiment, the display unit 120 also displays icons 70, 71, 72, 73, 74, 75, 76, and 77 at locations above, on the upper-right side of, on the right side of, on the lower-right side of, below, on the lower-left side of, on the left side of, and on the upper-left side of the current body type information 700. The user of the electronic device 100 may perform the input operation according to the icons 70-77, so as to observe other body type information. In the present exemplary embodiment, the locations above, on the upper-right side of, on the right side of, on the lower-right side of, below, on the lower-left side of, on the left side of, and on the upper-left side of the current body type information 700 may be collectively referred to as the "second locations". The second locations are adjacent or surround the current body type information 700 at the first location.

According to the present exemplary embodiment, the icons 70 and 74 are relevant to the amount of body fat, and the icons 72 and 76 are relevant to the amount of muscle. The functions of the icons 70 and 74 are the same as those of the icons 60 and 66; hence, no further explanation is given hereinafter. Similarly, the functions of the icons 72 and 76 are the same as those of the icons 64 and 62; hence, no further explanation is given hereinafter.

Specially, if the current body type information related to the user is the body type information M, the user may perform the input operation (e.g., clicking the icon 71) corresponding to the icon 71 through the input unit 140. The display unit 120 then displays the descriptions associated with the body type information I in the region 800. Here, the amount of body fat and the amount of muscle in the body type information I are both one level higher than those in the body type information M. Similarly, the user may perform the input operation (e.g., clicking the icon 73) corresponding to the icon 73 through the input unit 140. The display unit 120 then displays the descriptions associated with the body type information S in the region 800. Here, the amount of body fat in the body type information S is one level lower than that in the body type information M, but the amount of muscle in the body type information S is one level higher than that in the body type information M. The user may also perform the input operation (e.g., clicking the icon 75) corresponding to the icon 75 through the input unit 140. The display unit 120 then displays the descriptions associated with the body type information Q. Here, the amount of body fat and the amount of muscle in the body type information S are both one level lower than those in the body type information M. Similarly, the user may perform the input operation (e.g., clicking the icon 77) corresponding to the icon 77 through the input unit 140. The display unit 120 then displays the descriptions associated with the body type information G in the region 800. Here, the amount of body fat in the body type information G is one level higher than that in the body type information M, but the amount of muscle in the body type information G is one level lower than that in the body type information M. The input operations corresponding to the icons 70-74 may be performed together or individually, and the user can perform the input operations according to the icons 70-74 to observe other body type information and further select the target body type information.

Figures 8A, 8B:
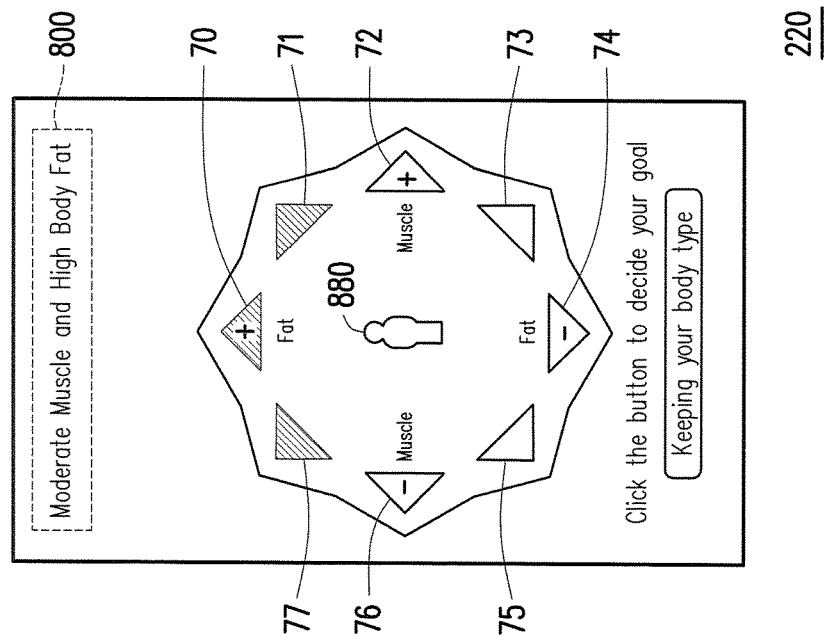
FIG. 8A and FIG. 8B are schematic diagrams of performing an input operation to observe other body type information according to an embodiment of the invention.

FIG. 8A and FIG. 8B are schematic diagrams of performing an input operation to observe other body type information according to an embodiment of the invention.

With reference to FIG. 8A and FIG. 8B that follow FIG. 7A and FIG. 7B, if the current body type information related to the user is the body type information M, the user may perform the first input operation through the input unit 140, as shown in FIG. 8A and FIG. 8B. In the present exemplary embodiment, the first input operation includes continuous input operations (e.g., clicking the icon 70 twice) corresponding to the icon 70.

According to the first input operation, the processing unit 160 enables the display unit 120 to display the body type information 880 corresponding to the body type information C (i.e., the first body type information) at the first location in the user interface 220 and display the descriptions associated with the body type information C in the region 800 in the user interface 210.

Note that the body type information C is on the edge of the matrix 200. There is no body type information on the upper-left side of, above, and on the upper-right side of the body type information C correspond to the icons 77, 70, and 71 in the user interface 210, and therefore the display unit 120 displays prompt information (i.e., the third prompt information) in the icons 77, 70, and 71, as shown in FIG. 8B. Namely, a body type information (i.e., the fifth body type information) in the matrix 200 fails to correspond to locations (i.e., the fifth locations) on the upper-left side of, above, and on the upper-right side of the body type information C, and therefore the display unit 120 displays the third prompt information in the icons 77, 70, and 71 corresponding to the fifth locations. Here, the prompt information is the blocks 77, 70, and 71 displayed in certain color. The way to display the prompt information far exceeds to what has been described herein. Particularly, in this exemplary embodiment, the icons 77, 70, and 71 may be collectively referred to as the "first icons".

Figures 9A, 9B:
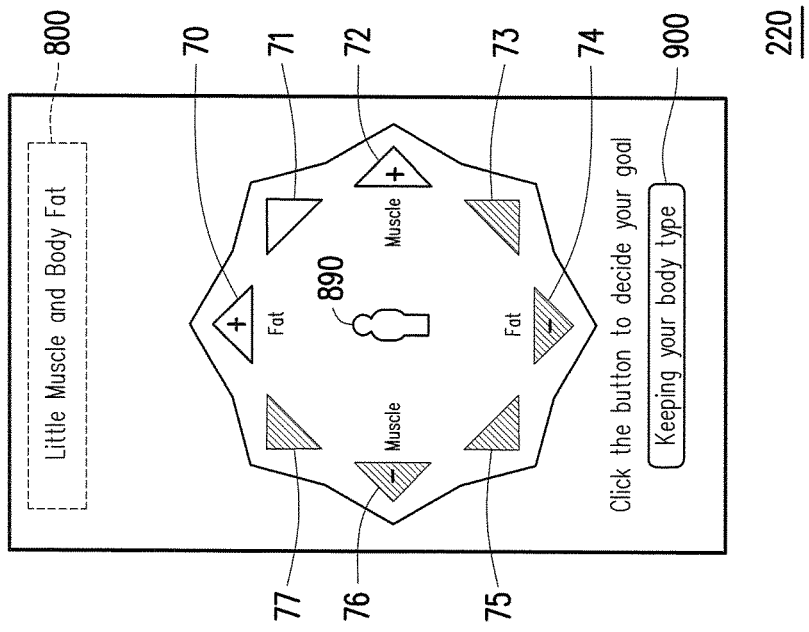
FIG. 9A and FIG. 9B are schematic diagrams of performing an input operation to observe other body type information according to an embodiment of the invention.

FIG. 9A and FIG. 9B are schematic diagrams of performing an input operation to observe other body type information according to an embodiment of the invention.

With reference to FIG. 9A and FIG. 9B that follow FIG. 7A and FIG. 7B, if the current body type information related to the user is the body type information M, the user may perform the input operation through the input unit 140, as shown in FIG. 9A and FIG. 9B. In the present exemplary embodiment, the input operation includes continuous input operations (e.g., clicking the icon 75 twice) corresponding to the icon 75.

According to the input operation, the processing unit 160 enables the display unit 120 to display the body type information 890 corresponding to the body type information U at the first location in the user interface 220 and display the descriptions associated with the body type information U in the region 800 in the user interface 220.

Note that the body type information U is in the corner of the matrix 200. There is no body type information on the upper-left side of, on the left side of, on the lower-left side of, below, and on the lower-right side of the body type information U correspond to the icons 77, 76, 75, 74, and 73 in the user interface 210, and therefore the display unit 120 displays prompt information in the icons 77, 76, 75, 74, and 73, as shown in FIG. 9A. Here, the prompt information is the icons 77, 76, 75, 74, and 73 displayed in certain color. The way to display the prompt information far exceeds to what has been described herein.

If the user intends to set the body type information U as the target body type information, the user may, for instance, click a button 900 displayed in the user interface 220 to perform the input operation. FIG. 10 is a schematic diagram of setting a target body type information according to an embodiment of the invention. With reference to FIG. 10 that follows FIG. 9A and FIG. 9B, after the user clicks the button 900 in the user interface 220, the display unit 140 may display the user interface 230 that includes a confirmation message 1000. When the user clicks the button 1001 (i.e., performs the second input operation) in the confirmation message 1000, the processing unit 160 may set the body type information U as the target body type information. When the user clicks the button 1002 in the confirmation message 1000, the processing unit 160 may return to the user interface 220 depicted in FIG. 9A, for instance.

Specially, after the user clicks the button 1001 in the confirmation message 1000 and sets the body type information U as the target body type information, the display unit 120 displays the current body type information 700 related to the user at the first location in the user interface 220, as shown in FIG. 7B. Besides, the icons 70-77 are displayed at the locations (i.e., the second locations) above, on the upper-right side of, on the right side of, on the lower-right side of, below, on the lower-left side of, on the left side of, and on the upper-left side of the current body type information 700. Moreover, since the user sets the body type information U as the target body type information, the display unit 120 further displays a prompt information (not shown, also referred to as the first prompt information) at the location (i.e., the third location) on the lower-left side (i.e., in the first direction) of the current body type information 700. The prompt information is displayed on the icon 75 or on the lower-left side of the current body type information 700 in FIG. 7B in another manner. The invention should not be limited thereto.

FIG. 11 is a schematic diagram of displaying a status information according to an embodiment of the invention.

With reference to FIG. 11, after the target body type information is set, the display unit 120 may further display a status information 1200 in the user interface 240. The status information 1200 represents a degree of completion achieved by changing from a body type corresponding to the current body type information (i.e., the body type information M) to a body type corresponding to the target body type information (i.e., the body type information U). In the present embodiment, the status information 1200 may be displayed in form of texts, figures, and percentages. However, the invention is not limited thereto, and the status information 1200 may also be displayed in another manner. In the present exemplary embodiment, the status information 1200 is displayed in the user interface 240 different from the user interface 220 depicted in FIG. 7B. However, the invention is not limited thereto, and the status information 1200 may also be displayed in the user interface 220 depicted in FIG. 7B, for instance.

Figure 12:
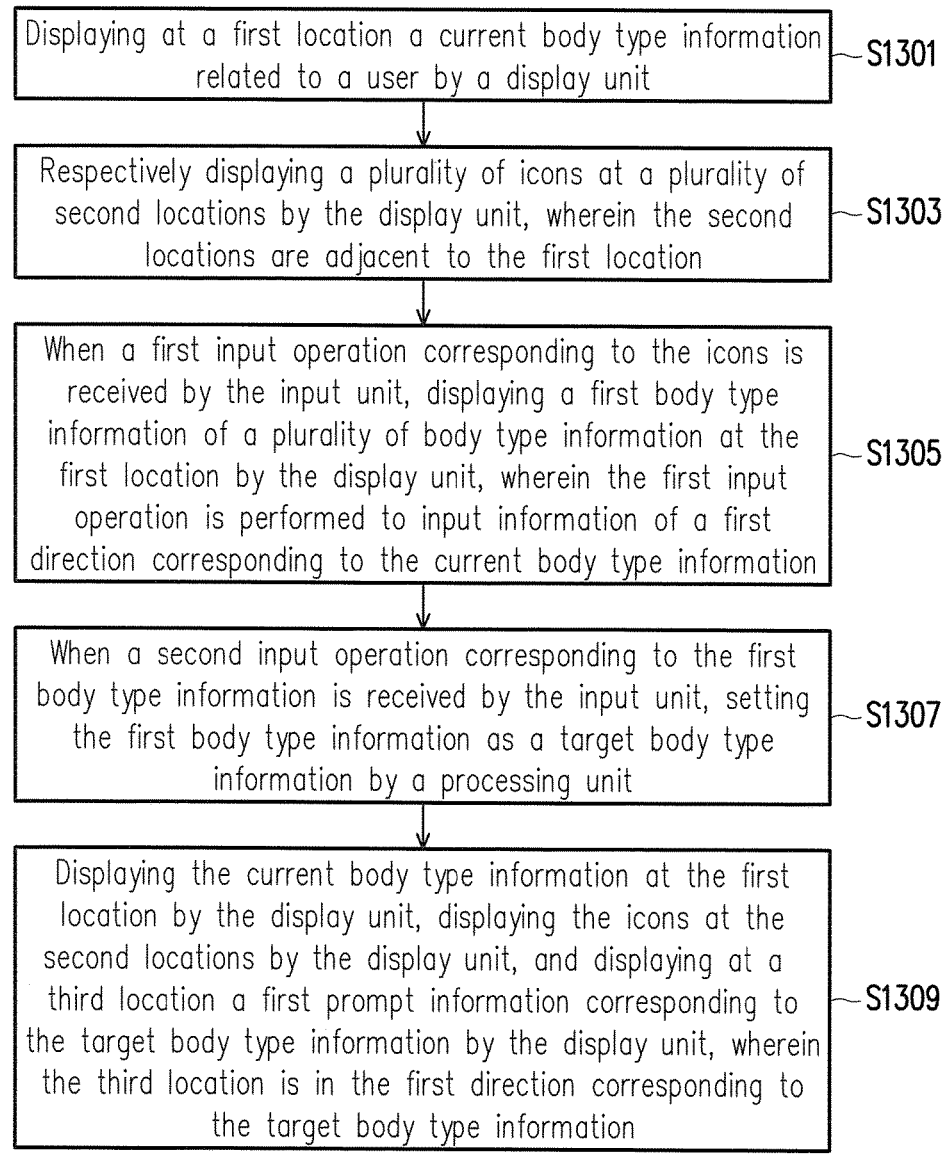
FIG. 12 is a flowchart of a user interface display method according to an embodiment of the invention.

FIG. 12 is a flowchart of a user interface display method according to an embodiment of the invention.

With reference to FIG. 12, in step S1301, the display unit 120 displays at the first location the current body type information related to the user. In step S1303, the display unit 120 respectively displays a plurality of icons at a plurality of second locations, and the second locations are adjacent to or surround the first location. When the input unit 140 receives the first input operation corresponding to the icons, in step S1305, the display unit 120 displays a first body type information of the plurality of body type information at the first location. Here, the first input operation is performed to input the first direction corresponding to the current body type information. After the input unit 140 receives a second input operation corresponding to the first body type information, in step S1307, the processing unit 160 sets the first body type information as the target body type information. In step S1309, the display unit 120 displays the current body type information at the first location, displays the icons at the second locations, and displays at a third location a first prompt information corresponding to the target body type information. Here, the third location is in the first direction corresponding to the target body type information.

In view of the above, the current body type information related to the user can be displayed in the user interface through performing the user interface display method provided herein. After the user sets up the target body type information, the current body type information related to the user and the prompt information related to the target body type information may be displayed in the user interface. Thereby, the user may know more about his or her body type and may be aware of how to change the current body type to the target body type (e.g., gain/lose body fat or gain/lose muscle mass). Besides, through applying the user interface display method, the status information is also displayed, such that the user s able to learn what should be done in order to obtain the target body type. To sum up, the user interface display method provided herein allows users to clearly know how to shape their bodies and assists the users in adjusting their body types to ideal body types in an effective manner.

It will be apparent to those skilled in the art that various modifications and variations can be made to the disclosed embodiments without departing from the scope or spirit of the invention. In view of the foregoing, it is intended that the invention covers modifications and variations of this disclosure provided that they fall within the scope of the following claims and their equivalents.

What is claimed is:

1. A user interface display method adapted for an electronic device, the electronic device comprising a display unit, an input unit, and a processing unit, the user interface display method comprising:
    storing a plurality of body type information into an n*n matrix, wherein each of a plurality of elements of the matrix corresponds to one of the plurality of body type information and n is a positive integer greater than 1;
    obtaining a current body type information corresponding to a physiological information of a user;
    setting the current body type information associated to one of the plurality of body type information in the matrix according to the physiological information by the processing unit;
    displaying at a first location the current body type information related to the user by the display unit;
    respectively displaying a plurality of icons at a plurality of second locations by the display unit, the plurality of second locations being adjacent to the first location, wherein the plurality of icons are corresponding to the plurality of body type information in the matrix around the current body type information;
    when a first input operation corresponding to the plurality of icons is received by the input unit, displaying a first body type information of the plurality of body type information in the matrix corresponding to the plurality of icons at the first location and the plurality of body type information in the matrix around the first body type information at the plurality of second locations by the display unit; and
    when a location at a plurality of locations or a block in a plurality of blocks fails to correspond to the plurality of body type information, displaying a prompt information by the display unit, wherein the prompt information is used to indicate that the location or the block cannot be set as a target body type information.

2. The user interface display method according to claim 1, wherein the first input operation is performed to input information of a first direction corresponding to the current body type information, and the user interface display method further comprises:
    when a second input operation corresponding to the first body type information is received by the input unit, setting the first body type information as a current the target body type information by the processing unit; and
    displaying the current body type information at the first location by the display unit, displaying the plurality of icons at the plurality of second locations by the display unit, and displaying at a third location a first prompt information corresponding to the target body type information by the display unit, wherein the third location is in the first direction corresponding to the current body type information.

3. The user interface display method according to claim 2, wherein the step of displaying at the first location the current body type information related to the user comprises:
    displaying by the display unit the current body type information in a first block at the first location; and
    respectively displaying a plurality of second body type information of the plurality of body type information in a plurality of second blocks at a plurality of fourth locations by the display unit, the plurality of the fourth locations being adjacent to the first location.

4. The user interface display method according to claim 3, the plurality of fourth locations comprising the plurality of second locations.

5. The user interface display method according to claim 4, wherein the step of respectively displaying the plurality of icons at the plurality of second locations comprises:
    respectively displaying the plurality of icons in a plurality of third blocks in the plurality of second blocks at the plurality of second locations by the display unit.

6. The user interface display method according to claim 5, further comprising:
    if a fourth block in the plurality of second blocks fails to correspond to a third body type information of the plurality of body type information, displaying a second prompt information in the fourth block by the display unit.

7. The user interface display method according to claim 3, wherein the step of displaying at the first location the first body type information of the plurality of body type information comprises:
    displaying by the display unit the first body type information in the first block; and
    respectively displaying by the display unit a plurality of fourth body type information of the plurality of the body type information in the plurality of second blocks.

8. The user interface display method according to claim 3, wherein the step of displaying the current body type information at the first location, displaying the plurality of icons at the plurality of second locations, and displaying at the third location the first prompt information corresponding to the target body type information comprises:

displaying by the display unit the current body type information in the first block;

respectively displaying by the display unit the plurality of second body type information of the plurality of body type information in the plurality of second blocks; and displaying by the display unit the first prompt information in a fifth block in the plurality of second blocks corresponding to the first direction of the current body type information.

9. The user interface display method according to claim 2, wherein the step of respectively displaying the plurality of icons at the plurality of second locations comprises:

if a fifth location at the plurality of second locations fails to correspond to a fifth body type information of the plurality of body type information, displaying a third prompt information on a first icon of the plurality of icons corresponding to the fifth location by the display unit.

10. The user interface display method according to claim 2, further comprising:

displaying a status information in form of a status bar by the display unit, wherein the status information represents a degree of completion achieved by changing from a first body type corresponding to the current body type information to a second body type corresponding to the target body type information.

\* \* \* \* \*